(12) United States Patent
Petignaud et al.

(10) Patent No.: US 9,804,421 B2
(45) Date of Patent: Oct. 31, 2017

(54) METHOD FOR DETERMINING AT LEAST ONE OPTICAL DESIGN PARAMETER FOR A PROGRESSIVE OPHTHALMIC LENS

(71) Applicant: ESSILOR INTERNATIONAL (COMPAGNIE GENERALE D'OPTIQUE), Charenton-le-Pont (FR)

(72) Inventors: Cécile Petignaud, Charenton-le-Pont (FR); Thierry Bonnin, Charenton-le-Pont (FR); Laurent Calixte, Charenton-le-Pont (FR); Sarah Marie, Charenton-le-Pont (FR)

(73) Assignee: ESSILOR INTERNATIONAL (COMPAGNIE GENERALE D'OPTIQUE), Charenton le Pont (FR)

( * ) Notice: Subject to any disclaimer, the term of this patent is extended or adjusted under 35 U.S.C. 154(b) by 0 days.

(21) Appl. No.: 15/035,068

(22) PCT Filed: Oct. 30, 2014

(86) PCT No.: PCT/FR2014/052761
§ 371 (c)(1),
(2) Date: May 6, 2016

(87) PCT Pub. No.: WO2015/067877
PCT Pub. Date: May 14, 2015

(65) Prior Publication Data
US 2016/0274383 A1     Sep. 22, 2016

(30) Foreign Application Priority Data
Nov. 8, 2013  (FR) .................... 13 60990

(51) Int. Cl.
*A61B 3/10*   (2006.01)
*A61B 3/00*   (2006.01)
(Continued)

(52) U.S. Cl.
CPC .......... *G02C 13/005* (2013.01); *A61B 3/0025* (2013.01); *A61B 3/113* (2013.01);
(Continued)

(58) Field of Classification Search
USPC ................................................. 351/200–246
See application file for complete search history.

(56) References Cited

U.S. PATENT DOCUMENTS 6,827,443 B2 * 12/2004 Fisher ................ A61B 3/113
                                               351/209
7,992,997 B2 *  8/2011 Varnas ................. G02C 7/027
                                               351/159.42
8,297,752 B2    10/2012 Wada

FOREIGN PATENT DOCUMENTS

FR        2 898 993        9/2007
FR        2 911 696        7/2008
(Continued)

*Primary Examiner* — Mohammed Hasan
(74) *Attorney, Agent, or Firm* — Cozen O'Connor

(57) ABSTRACT

A method for determining at least one optical conception parameter for a progressive ophthalmic lens intended to equip a frame of a wearer, depending on the visual behavior of the latter. The method comprises the following steps: a) collecting a plurality of behavioral measurements relating to a plurality of gaze directions and/or positions of the wearer during a visual task; b) statistically processing said plurality of behavioral measurements in order to determine a zone of use of the area of an eyeglass fitted in said frame, said zone of use being representative of a statistical spatial distribution of said plurality of behavioral measurements; and c) determining at least one optical conception parameter for said progressive ophthalmic lens depending on a spatial extent and/or position of the zone of use.

19 Claims, 5 Drawing Sheets

(51) Int. Cl.
*G02C 13/00* (2006.01)
*A61B 3/113* (2006.01)
*G02C 7/02* (2006.01)
*G02C 7/06* (2006.01)

(52) U.S. Cl.
CPC ............. *G02C 7/027* (2013.01); *G02C 7/063* (2013.01); *G02C 7/066* (2013.01)

(56) References Cited

FOREIGN PATENT DOCUMENTS

| | | |
|---|---|---|
| FR | 2 924 824 | 6/2009 |
| FR | 2 965 364 | 3/2012 |
| KR | 101 300 670 | 8/2013 |

* cited by examiner

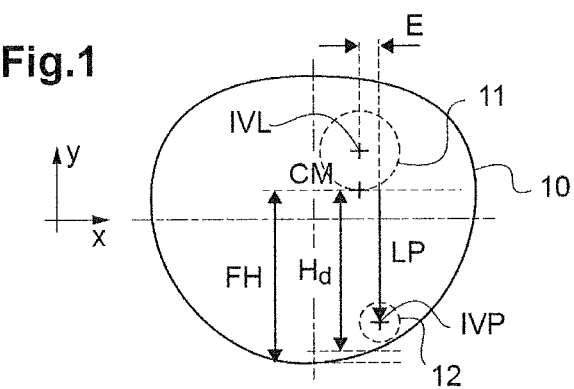
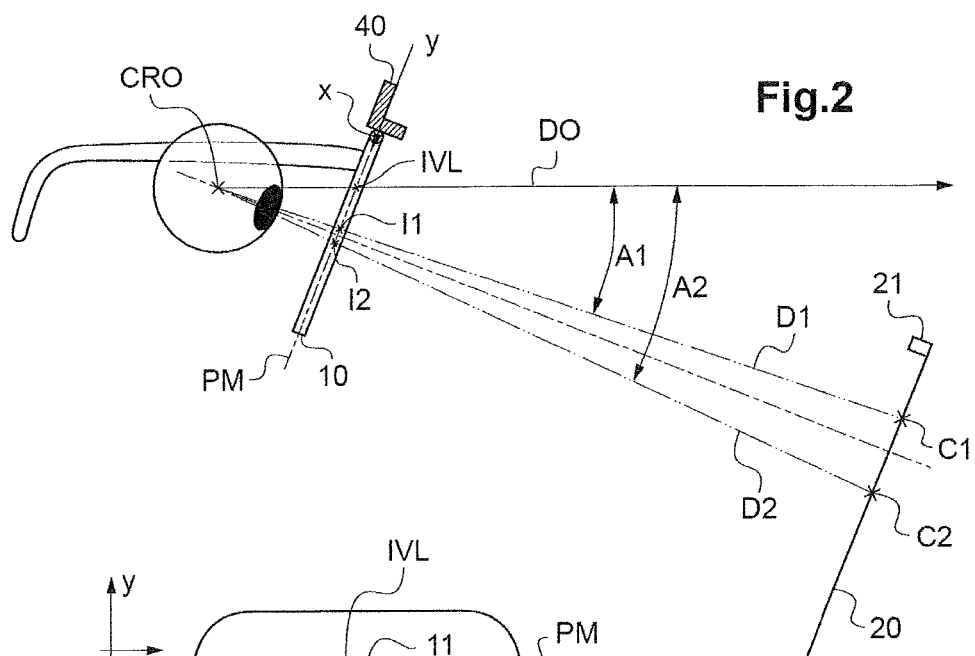
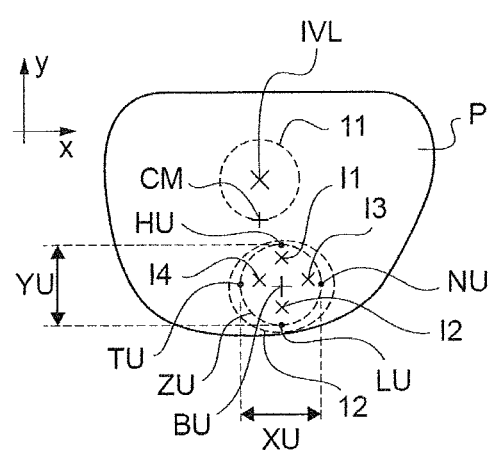

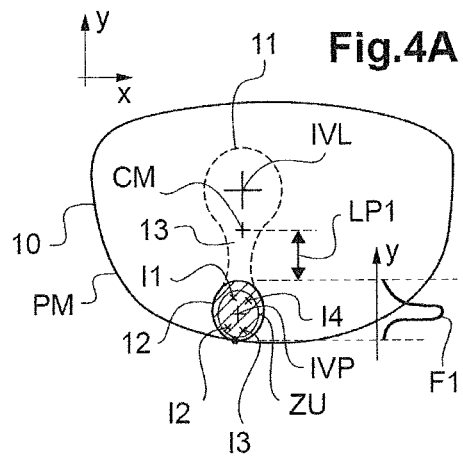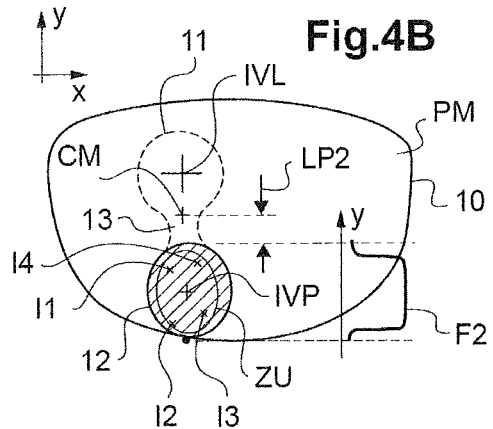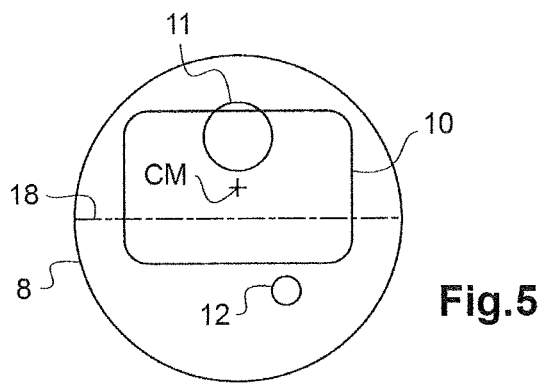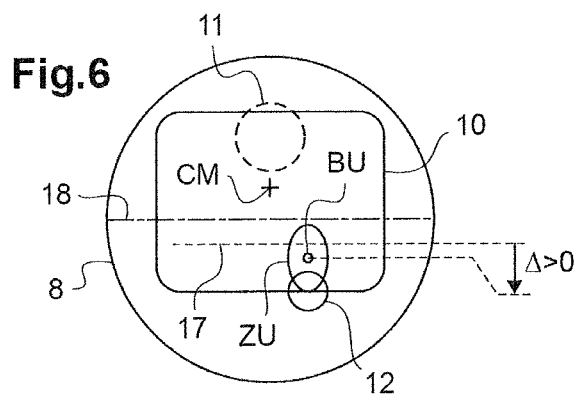

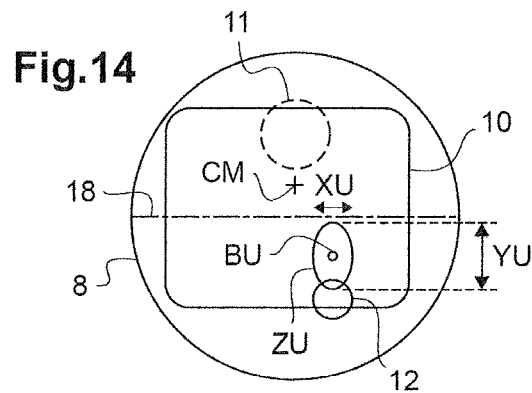
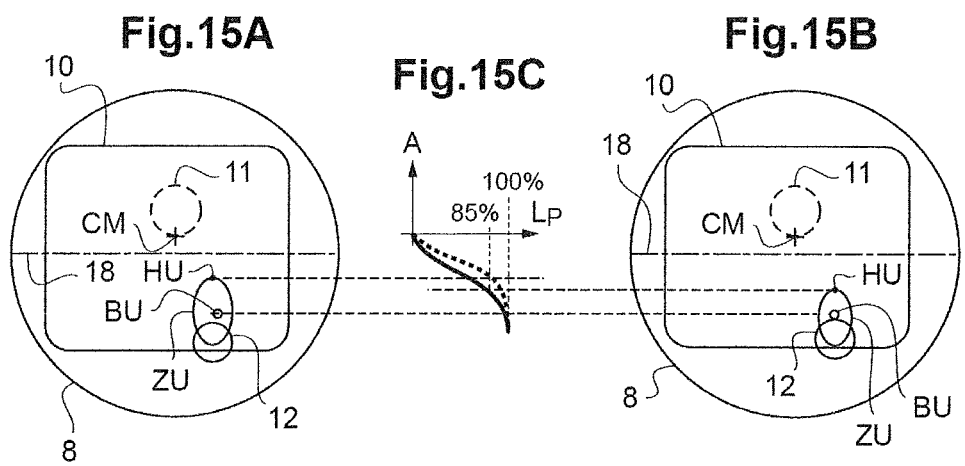
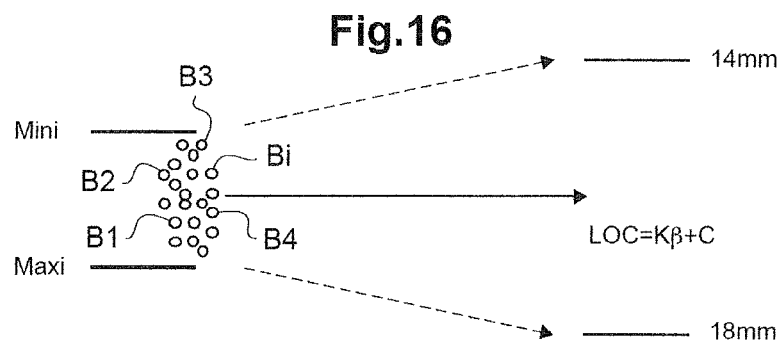

METHOD FOR DETERMINING AT LEAST ONE OPTICAL DESIGN PARAMETER FOR A PROGRESSIVE OPHTHALMIC LENS

RELATED APPLICATIONS

This is a U.S. National Phase Application under 35 USC 371 of International Application PCT/FR2014/052761 filed on Oct. 30, 2014.

This application claims the priority of French application no. 1360990 filed Nov. 8, 2013, the entire content of which is hereby incorporated by reference.

TECHNICAL FIELD TO WHICH THE INVENTION RELATES

The present invention relates to a method for determining at least one optical conception parameter of a progressive ophthalmic lens for visual-correction spectacles.

It in particular relates to a method for determining a personalized parameter for progression length, internal offset, progression profile and/or extent of a vision zone for a progressive ophthalmic lens.

It moreover relates to a method for selecting an ophthalmic lens suitable for the needs of the wearer and for a specific frame chosen by a particular wearer.

TECHNOLOGICAL BACKGROUND

FIG. 1 schematically shows a progressive ophthalmic lens 8 in projection in the mean plane of the frame 10. The expression "progressive lens" (or "progressive eyeglass") is understood to mean an ophthalmic lens with a progressive cylindrical and/or spherical power addition for visual-correction spectacles. The progressive lens includes, in its upper portion, a far-vision zone 11 the optical power of which is suitable for the far vision of the wearer depending on his visual-correction needs and, in its lower portion, a near-vision zone 12 the optical power of which is suitable for the near vision of this wearer.

As is known, between the far-vision (or FV) zone 11 and the near-vision (or NV) zone 12 there is a vision zone suitable for intermediate-distance vision (or IV, not illustrated).

The reference point IVL is a far-vision point defined by the manufacturer, for example at the center of a circle delimiting the far-vision zone 11. Likewise, the reference point IVP is a near-vision point defined by the manufacturer, for example at the center of a circle delimiting the near-vision zone 12.

Standard ISO 13666:2012 defines certain parameters used for the fitting of a progressive lens. Thus, the fitting point CM is a point located on the front surface of an eyeglass or a semi-finished eyeglass, that the manufacture considers to be a reference point for the positioning of the eyeglass in front of the eye. The fitting point CM is in general marked by an erasable marking that is removed after fitting. The fitting height FH is the vertical distance that separates the fitting point CM from the horizontal tangent passing through the bottom point of the periphery of the edged lens, i.e. through the lowest point of the interior outline of the rim of the frame. The datum height (Hd) is the vertical distance between the fitting point CM and that point of the frame 10 which is located vertically under the fitting point CM. The datum height Hd is smaller than or equal to the fitting height FH, depending on the shape of the edged lens (which corresponds, when the frame is a full-rimmed frame, to the shape of the interior outline of the corresponding rim of the frame 10).

A progression length (LP or LOC for length of corridor) is also defined as the vertical distance between the fitting cross and the position of the point IVP.

Moreover, the internal offset (or inset E) of the lens is defined as the horizontal offset between the far-vision reference point IVL and the near-vision reference point IVP.

The optical power of the lens varies, preferably continuously, between said far-vision reference point IVL and said near-vision reference point IVP, along a (jagged or curved) line called the principal progression meridian line, which passes through these two points. This principal progression meridian line passes through the three FV, IV and NV zones in an overall vertical direction.

The conception of a progressive lens especially aims to determine the position of the points IVL and IVP, the position and extent of the far-vision zone 11, the position and extent of the near-vision zone 12, the value of the internal offset E and the progression profile of the optical power addition along the principal progression meridian line.

The choice of a frame places certain constraints for example on the determination of the progression length Lp.

The optician in general determines values of progression length and of position of the FV and NV zones during optical spectacle-fitting measurements, for example acquired on an apparatus of the type sold under the trademark Visioffice.

Customarily, the choice of the progression length is made by the optician on the basis of subjective criteria such as the posture of the wearer or feedback given by the latter on his preceding piece of equipment.

A method for determining the progression length of a lens is also known from document U.S. Pat. No. 8,297,752, in which method a single far-vision point of the wearer and a single near-vision point of the wearer are determined on the ophthalmic lens and a corresponding progression length is deduced therefrom. An ophthalmic lens suitable for the wearer may thus be selected.

However, depending on the shape of the rims of the frame, it is not certain, by applying this method, that all the zone for near vision used by the wearer will be included in the ophthalmic lens once the latter has been edged and fitted in the frame chosen by the wearer.

SUMMARY OF THE INVENTION

In order to improve the visual comfort of a wearer equipped with a progressive ophthalmic lens, it is desirable to adjust at least one optical conception parameter of a progressive ophthalmic lens depending on the visual behavior of the wearer, on his natural posture for a visual task and on the frame chosen by the wearer.

In the present document, the expression "optical conception parameter of a progressive ophthalmic lens" is understood to mean one or more parameters that make it possible to determine:
  the optical design of the ophthalmic lens, i.e. the spatial distribution of spherical and/or cylindrical power over the lens. Optical design in particular covers the spatial delimitation of the near-vision zone and of the far-vision zone; and/or
  the spatial distribution of prismatic deviations of the eyeglass, liable to affect the natural direction of the gaze.

The optical conception parameter(s) of a progressive ophthalmic lens are then used to select a progressive ophthalmic lens from a range of lenses proposed by a manufacturer or to determine the surface to be machined of one or both faces of the lens so as to manufacture the progressive ophthalmic lens suitable for the wearer.

In order to remedy the aforementioned drawback of the prior art, one aspect of the present invention is directed to a method for determining at least one optical conception parameter for a progressive ophthalmic lens intended to equip a frame of a wearer, depending on the visual behavior of the latter.

More particularly, a method according to an aspect of the invention comprises the following steps:

a) collecting a plurality of behavioral measurements relating to a plurality of gaze directions and/or positions of the wearer during a visual task;

b) statistically processing said plurality of behavioral measurements in order to determine a zone of use of the area of an eyeglass fitted in said frame, said zone of use (ZU) being representative of a statistical spatial distribution of said plurality of behavioral measurements; and c) determining at least one optical conception parameter for said progressive ophthalmic lens depending on a spatial extent and/or position of the zone of use.

The following are other nonlimiting and advantageous features of an embodiment of the method according to the invention:

said at least one optical conception parameter comprises at least one optical conception parameter of the design of said progressive ophthalmic lens among a restricted progression-length range [Lpmin; Lpmax], a progression length, a height of the near-vision zone, a width of the near-vision zone, and an internal offset of said progressive ophthalmic lens;

said at least one optical conception parameter comprises a profile of progression of the optical power along a meridian between the far-vision zone and the near-vision zone for said progressive ophthalmic lens.

Advantageously, according to an embodiment of the invention the method for determining at least one optical conception parameter for a progressive ophthalmic lens furthermore comprises the following steps:

b1) calculating a position of the centroid of the zone of use; and c1) determining a restricted progression-length range or a value of progression length depending on the position of the centroid of the zone of use.

In one particular embodiment, the method furthermore comprises the following steps:

b2) determining the sign of the difference $\Delta$ between the vertical position of the centroid and a reference vertical position, corresponding to a mean drop angle of the gaze relative to a primary direction of the far-vision gaze of the wearer; and c2) determining a restricted progression-length range or a value of progression length depending on the sign of the difference $\Delta$.

In another particular embodiment, the method furthermore comprises the following steps:

a3) acquiring a measurement of fitting height for said progressive ophthalmic lens in said frame;

b3) calculating the value of the difference $\Delta$ between the vertical position of the centroid (BU) and a reference vertical position, corresponding to a mean drop angle of the gaze relative to a primary direction of the far-vision gaze of the wearer; and c3) determining a value of progression length depending on said measurement of fitting height and on said value of the difference $\Delta$.

According to one variant of this embodiment, in step c3) a value of progression length is determined, said value being equal to the fitting height decreased by a correction function $\epsilon$, where $\epsilon$ is a function of the difference $\Delta$, of the fitting height, of a measurement of ocular refraction of the wearer and/or of the zone of use.

In another particular embodiment, the method furthermore comprises the following steps:

a4) acquiring a measurement of fitting height for said progressive ophthalmic lens in said frame;

b4) calculating the value of the difference $\Delta$ between the vertical position of the centroid (BU) and a reference vertical position, corresponding to a mean drop angle of the gaze relative to a primary direction of the far-vision gaze of the wearer; and b5) calculating at least one value representative of a dispersion of the zone of use; and c5) determining a value of progression length depending on said measurement of fitting height, on said value of the difference and/or on said at least one value representative of a dispersion of the zone of use.

Advantageously, in step c5) a value of progression length is determined, said value being equal to the fitting height decreased by a correction function $\epsilon$ where $\epsilon$ is a function of the difference $\Delta$, of the fitting height and of the dispersion of the zone of use.

In another particular embodiment, the method furthermore comprises the following steps:

b6) calculating the position of a limit of the zone of use; and c6) determining a progression profile of the optical power along a meridian between the far-vision zone and the near-vision zone depending on the position of said limit of the zone of use.

In another particular embodiment, the method furthermore comprises the following steps:

b7) calculating the position of a limit of the zone of use; and c7) determining the value of the internal offset depending on the position of said limit of the zone of use.

In another particular embodiment, the method furthermore comprises the following steps:

b8) calculating a position of the centroid of the zone of use and a vertical spread of the zone of use; and c8) determining the height of the near-vision zone depending on the position of the centroid of the zone of use and on the vertical spread of the zone of use.

In another particular embodiment, the method furthermore comprises the following steps:

b9) calculating a horizontal spread of the zone of use; and c9) determining the width of the near-vision zone depending on the horizontal spread of the zone of use.

Particularly and advantageously, the optical conception parameter is adjusted depending on the spherical-compensation value of the prescription of the progressive ophthalmic lens and/or on the value of the optical-power addition between the far-vision zone and the near-vision zone, and/or depending on a measurement of an angle of inclination of the head of the wearer.

In another particular embodiment, the method furthermore comprises the following steps:

d) a plurality of mean values relating to an area of use are provided, said values being associated with a plurality of reference wearers;

e) said plurality of mean values associated with said plurality of reference wearers are statistically processed in order to determine a statistical distribution of said plurality of mean values;

f) a mean value relating to the area of use is determined for a wearer during said visual task; and g) at least one optical conception parameter is determined for a progressive ophthalmic lens for said wearer depending on said mean value relating to the area of use for said wearer and on said statistical distribution of mean values associated with said plurality of reference wearers.

Another aspect of the invention relates to a method for selecting a progressive ophthalmic lens intended for a wearer comprising the following steps:

determining at least one optical conception parameter by implementing a determining method according to one of the above embodiments; and selecting, from a standard set of lenses, a progressive ophthalmic lens depending on the determined optical conception parameter.

Another aspect of the invention relates to a method for determining a progressive ophthalmic lens intended for a wearer comprising the following steps:

choosing at least one current surface of an ophthalmic lens;

determining at least one optical target conception parameter by implementing a determining method according to one of the described embodiments; and determining said progressive ophthalmic lens by optimizing, under the conditions of wear, the current surface of said ophthalmic lens using the determined optical target.

Another aspect of the invention relates to a method for manufacturing a progressive ophthalmic lens comprising the following steps:

providing an initial lens;

determining the progressive ophthalmic lens by implementing the method for determining a progressive ophthalmic lens described above; and machining the initial lens in order to produce said progressive ophthalmic lens.

Another aspect of the invention relates to a progressive ophthalmic lens personalized for a wearer, said progressive ophthalmic lens having at least one optical conception parameter determined depending on a zone of use by implementing a determining method according to one of the described embodiments.

BRIEF DESCRIPTION OF THE DRAWINGS

The description which follows with reference to the appended drawings, which are given by way of nonlimiting examples, will make it easy to understand the essence of the invention and how it can be achieved.

In the appended drawings:

FIG. 1 shows a progressive lens seen from in front and various used parameters;

FIG. 2 shows a side view of an example of a system for acquiring behavioral measurements on the eye of a wearer during certain near-vision visual tasks;

FIG. 3 graphically shows a zone of use ZU taking the form of an area in projection in the plane of the frame;

FIGS. 4A and 4B show in projection in the mean plane of the frame behavioral measurements for two different wearers and a statistical distribution associated respectively with these behavioral measurements;

FIG. 5 shows a progressive lens seen from in front and a first mode of comparison of a frame with a progressive eyeglass design;

FIG. 6 shows a first variant of the first embodiment for determining a progression length of a progressive lens;

FIG. 14 illustrates one embodiment for determining the extent of the NV zone of use of a progressive lens;

FIG. 15 illustrates examples of determination of the progression profile of the optical power between the FV zone and the NV zone;

FIG. 16 illustrates another embodiment for determining a progression length of a progressive lens depending on measurements carried out on a reference population.

DETAILED DESCRIPTION OF THE DRAWINGS

Device

Figure 7:
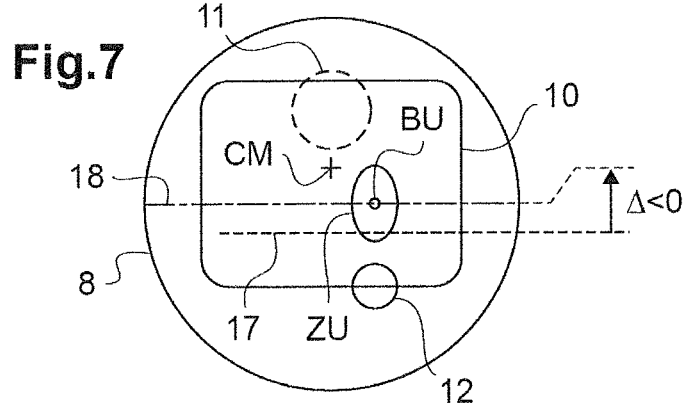
FIG. 7 shows a second variant of the first embodiment for determining a progression length of a progressive lens.

FIG. 2 shows a side view of a system for acquiring behavioral measurements on the eye of a wearer during certain near-vision visual tasks.

FIG. 2 is a representation in projection in the sagittal plane of the wearer. The plane of FIG. 2 is preferably a vertical plane.

Preferably, the wearer is equipped with a frame 10 that he has chosen, with no lens fitted in the interior.

It is possible to envision placing a frame other than that chosen, preferably having dimensions larger than that chosen so that the gaze of the wearer is not constrained by the edges of the frame.

It is also possible to envision placing the chosen frame with presentation lenses, having no power, or with corrective lenses, for example lenses similar to those that the wearer currently uses, lenses with unifocal correction or lenses with progressive correction.

The frame 10 is preferably equipped with a locating system 40 intended to allow the position of the head of the wearer in space to be determined from a captured image of the head of the wearer equipped with the locating system. This locating system is described in detail in document FR2914173, page 7, line 5 to page 10, line 8. It will therefore not be described in more detail here.

The locating system 40 has well-known geometric characteristics, which allow, from a captured image of the head of the wearer, in which image this locating system appears, the position of the head of the wearer in space to be determined in a frame of reference associated with this image-capturing device.

To execute a visual task, the wearer is presented with a medium 20 (FIG. 2) that he may for example hold between his hands and place in the way that he desires relative to his head.

This medium 20 is preferably a flat medium including a digital display portion. It is for example a touch tablet.

This medium 20 generally includes a target C1, C2 that the wearer must follow with his gaze during the task that is assigned to him.

The visual task is for example a pursuit task during which the wearer follows with his eyes the movements of the target C1, C2.

In order to allow the directions of the gaze of the wearer to be determined while the latter is executing the visual task that has been assigned to him, the medium 20 includes at least one image-capturing device 21. It is preferably a video camera in order to acquire a video of the wearer during the visual task.

The position of the target C1, C2 that the wearer follows with his eyes during the visual task is known at every instant relative to the medium 20. Said position is therefore known in a frame of reference associated with the image-capturing device 21.

Thus, by virtue of this arrangement, the position of the target C1, C2 on which the gaze of the wearer is fixated at the moment of the image capture is known in a frame of reference associated with the image-capturing device.

The image-capturing apparatus 21 makes it possible to capture an image of the head of the wearer for various positions of the target C1, C2 corresponding to various gaze directions D1, D2.

Advantageously, the image acquisition may be carried out via the recording of a video.

The captured images of the head of the wearer are transmitted to an information-processing unit that may be integrated into the medium or be remote.

The captured images may be processed in real-time or after all the images have been captured.

Thus, the information-processing unit deduces therefrom the direction of the gaze D1, D2 of the wearer during each image capture as being the straight line connecting the eye rotation center CRO to the target C1, C2 in its corresponding position during the image capture.

The information-processing unit then allows the position of the point of intersection I1, I2, I3, I4 of the direction of the gaze D1, D2 of the wearer and of a surface PM associated with said frame 10 to be determined. Advantageously, the surface PM is the mean plane of the rim of the frame.

More precisely, the information-processing unit determines the coordinates (x, y) of each point of intersection I1, I2 of the gaze direction D1, D2 and the mean plane PM of the rim of the frame 10 in an orthonormal coordinate system (X, Y) of this mean plane PM.

FIG. 2 illustrates an exemplary device suitable for acquiring a set of measurements of directions of the near-vision gaze and for calculating the positions of the points of intersection I1, I2 of the gaze direction D1, D2 and the mean plane PM of the rim of the frame 10.

Alternatively, the device in FIG. 2 may be used to acquire a set of measurements of the drop angle (A1, A2) of the gaze of the wearer between a primary direction D0 of the far-vision gaze of the wearer and a plurality of near-vision gaze directions D1 and D2 for various positions of the target C1, C2, respectively. The measurement of the drop angle of the gaze is taken in the sagittal plane of the wearer (plane in FIG. 2), the sagittal plane preferably being vertical during the measurements.

Devices other than the devices in FIG. 2 may be used to acquire the behavioral measurements used in the context of the present invention.

Advantageously, the measuring device records the time spent by the wearer in each gaze direction corresponding to one measurement.

One and the same measuring device or a plurality of optical spectacle-fitting or eye-test devices may be used to collect complementary measurements relating to the cephalic posture of the wearer and/or the bodily posture of the wearer, a posture being associated with each measurement of the plurality of measurements of direction, position and/or drop angle of the near-vision gaze of the wearer.

Method

Step a)

A set of behavioral measurements relating to a wearer are acquired, comprising a plurality of measurements of directions of the gaze, a plurality of positions of points of intersection I1, I2 of directions of the gaze with a plane or a determined surface and/or a plurality of measurements of the drop angle (A1, A2) of the gaze of the wearer.

In a first example, the wearer is placed in a situation in which he carries out a visual task, for example visual pursuit or reading, in a determined vision posture, for example facing a system for acquiring behavioral measurements on the eye of a wearer, such as illustrated with regard to FIG. 2.

In another example, the behavioral measurements relating to a wearer may originate from a computerized recording.

In the examples described below, said plurality of behavioral measurements relates to near vision.

Advantageously, the number of measurements of the plurality of behavioral measurements is sufficient to form a statistically significant sample. Preferably, this number of measurements is higher than or equal to one or a few tens or a few hundred.

As indicated above, the set of behavioral measurements may be acquired by any known measuring system. Thus, the measuring system illustrated in FIG. 2 is one example, but another measuring system may be based on the use of a temporary or permanent eye-tracking device allowing data on the eye of the wearer during certain visual tasks to be acquired. The way in which the measurements of the positions of the points of intersection are acquired is nonlimiting.

Complementarily, in addition to the behavioral measurements, ophthalmic correction prescription data associated with the wearer, framing data associated with the chosen frame and/or data relating to the spherical power addition profile are acquired.

Preferably, behavioral measurements relating to a wearer, data associated with the chosen frame and data relating to the prescription of the wearer are acquired.

The set of starting data for example comprises:

1—a set of behavioral measurements, comprising a plurality of measurements of directions of the near-vision gaze, a plurality of positions of points of intersection I1, I2 of directions of the near-vision gaze with a plane or a surface and/or a plurality of measurements of the drop angle (A1, A2) of the near-vision gaze of the wearer;

2—a fitting height (FH);

3—data relating to the shape of the frame (extraction of the datum fitting height Hd);

4—an ophthalmic correction prescription of the wearer; and

5—a design of the adopted spherical power addition profile.

This starting set is then exploited during the steps b) of processing in order to determine a zone of use and c) of determining at least one optical conception parameter for a progressive ophthalmic lens.

Step b) Statistical Processing

Next, the set of behavioral measurements is processed to determine a zone of use (ZU) representative of a statistical distribution of said plurality of measurements, for example in near vision.

In the present document, a zone of use ZU or zone of travel of an eyeglass is defined as being a zone of space representative of a statistical distribution of a set of points on the eyeglass through which the gaze of the wearer passes during a particular visual task, for a conventional use or for a given distance. The zone of use ZU may be defined equivalently either spatially, by a statistical distribution of points (I1, I2) on the eyeglass or on another projection plane, or vectorially, by a statistical distribution of directions of the gaze (D1, D2). Alternatively and more simply, the zone of use ZU may also be defined in tabulated format by a statistical distribution of the drop angles of the gaze (A1, A2) in the sagittal plane of the wearer.

In one particular case, the zone of use ZU may be limited to near vision.

Preferably, the zone of use ZU is represented in graphical form by an area (FIG. 3) in projection in the plane of the frame (PM). In another embodiment, it is possible to take a projection plane other than that associated with the eyeglass. By way of example, it is possible to use a projection plane other than that of the points of intersection I1, I2 on the eyeglass, such as any virtual plane or the plane of the target 20.

More precisely, all the coordinates (x, y) of the behavioral measurement points, comprising the plurality of positions of points of intersection (I1, I2, I3, I4) of the directions of the gaze with the plane of the frame PM or another projection plane, are collected.

In step b), all of the coordinates (x, y) of the plurality of behavioral measurement points are statistically processed so as to determine a distribution in the statistical sense of the measurement points. Advantageously, a processing step is carried out beforehand, for example in order to suppress aberrant points and/or to take into account only 95% of the measured points. The statistical distribution for example comprises a mean position (in x and/or in y) of the set of measured points, a position of the centroid BU (in x and/or in y) of the set of measured points, a horizontal standard deviation, a vertical standard deviation and/or other parameters of the statistical distribution of the behavioral measurements. In one embodiment, the calculation of the centroid corresponds to the calculation of the mean position of the set of measured points, each measured point being weighted by a weighting coefficient equal to 1. Thus, the centroid represents the mean of the gaze directions. In another embodiment, the calculation of the centroid takes into account a weighting coefficient associated with each measurement point; for example, the weighting coefficient associated with each measurement point may be a coefficient related to the time spent by the wearer at each measurement point. More precisely, the time spent per unit area may be used as a weighting coefficient to weight the zone of use ZU in terms of spread. For example, a useful area of the zone of use, which corresponds for example to 80% of the time spent, is weighted. Thus, the area of use is considerably smaller and does not have the same impact in a given equation featuring the zone of use ZU compared to a zone of use of uniform weighting, the position of the centroid and/or the extent of the zone of use being affected by the weighting coefficients.

From this statistical distribution, a zone of use ZU is determined, represented for example by an area, defined by the position of the centroid BU of the set of NV points measured, the shape of this area, which is for example circular, elliptical or any other shape, the spatial extent in one or two spatial dimensions XU and/or YU (depending on the horizontal and/or vertical standard deviation) and/or by high, low, nasal and/or temporal limits HU, LU, NU, TU. The spread of the zone of use represents the area covered by the ocular movements during the behavioral measurements. The spread of the zone of use is defined by a height YU and a width XU, and optionally an orientation. The temporal apportionment or distribution in the zone of use represents the time spent by the wearer per unit area of the zone of use. In general, this temporal apportionment or distribution is Gaussian and centered on the centroid BU of the zone of use ZU. However, in certain particular cases, a bimodal temporal apportionment or distribution having two local maxima in the zone of use is observed.

Step b) thus makes it possible to determine the spatial extent (shape and size) of the zone of use relative to the points of intersection: an area, of any shape, encircling all the points of intersection, or an area having a standard deviation in two dimensions.

By way of nonlimiting example, the zone of use is represented by an ellipse containing a predetermined percentage of measured points of intersection, preferably 95% of the points of intersection.

Since the zone of use is a statistical representation of the measurements, this zone of use does not necessarily contain all of the measurements.

The statistical processing may allow aberrant measurements to be eliminated.

In one exemplary embodiment, the statistical processing of the behavioral measurements makes it possible to determine:

a position (X, Y) of the centroid (BU) of the zone of use (ZU);

a vertical spread (YU) and a horizontal spread (XU) of the zone of use (95% of the measurement points); and/or an apportionment or distribution of the time spent per unit area in the zone of use.

In another exemplary embodiment, a plurality of measurements of the direction of the gaze D1, D2 of the wearer is used, and this plurality of measurements of the direction of the gaze is statistically processed to determine a vectorial statistical distribution of the plurality of measurements of the direction of the gaze.

Thus, the statistical processing of the plurality of measurements of the direction of the gaze makes it possible to determine a statistical distribution defined by:

a mean gaze direction of the wearer;

a centroidal gaze direction of the wearer;

a vertical standard deviation of the gaze direction of the wearer; and/or a horizontal standard deviation of the gaze direction of the wearer, etc.

From this statistical distribution of the plurality of measurements of the direction of the gaze, a two- or three-dimensional zone of use is determined, defined for example by:

a mean gaze direction of the wearer;

a standard deviation about the mean gaze direction of the wearer;

a high gaze direction of the wearer;

a low gaze direction of the wearer;

a maximum convergence gaze direction of the wearer; and/or a maximum divergence gaze direction of the wearer; and the time spent per unit solid angle in the zone of use.

In one variant, a projection of the plurality of measurements of the direction of the gaze D1, D2 of the wearer onto the plane of the frame (PM) or onto another plane is determined, this amounting to processing of the plurality of measurement points described above.

Alternatively and more simply, the plurality of behavioral measurements includes a plurality of measurements of the drop angle of the gaze (A1, A2) in the sagittal plane of the wearer. In this case, the statistical processing allows a statistical distribution of the plurality of measurements of the drop angle of the gaze to be determined. The zone of use ZU may then be represented by a table for example comprising a mean value of the drop angle of the gaze, a centroid of the drop angle of the gaze, a standard deviation of the drop angle of the gaze, and a low value and/or a high value of the drop angle of the gaze. In this simplified embodiment, it is thus not necessary to graphically trace the zone of use.

FIG. 4A and FIG. 4B respectively show an example of behavioral measurements of the points of intersection (I1, I2, I3, I4) between the direction of the gaze in the mean plane of the frame for a first wearer and a second wearer, respectively, in a near-vision posture.

It will be noted that identical or corresponding elements of the various ophthalmic lenses shown in projection in the mean plane of the frame in FIGS. 4A and 4B are indicated by the same reference signs.

Large behavioral variations are observed from one wearer to another for a given FV and NV compensation.

In general, the mean drop of the gaze to pass from FV to NV is comprised between 15 and 21 degrees and preferably is 20 degrees. This mean drop of the gaze corresponds to a mean drop that is comfortable for the wearer, i.e. to a rest position for the gaze of the wearer. However, with certain wearers a mean drop of the gaze different from this reference value of 20 degrees is observed. Lastly, with certain wearers a very much larger spatial dispersion in the measurements is observed than with other wearers. This may be explained by the fact that, during a given visual pursuit task, each wearer accompanies the movements of the eyes with relatively large movements of the head. However, it is not essential, in the method of the invention, to measure the cephalic movements associated with each measurement of position, direction or drop of the gaze.

Thus, in FIG. 4A, it may be seen that the spatial distribution of the points of intersection I1, I2, I3, I4 is quite narrow about the near-vision point IVP. In contrast, in FIG. 4B, it may be seen that the spatial distribution of the points of intersection I1, I2, I3, I4 is more spread out about the near-vision point IVP.

In each of FIGS. 4A and 4B, respectively, has been shown the zone of use ZU corresponding to the statistical processing of the measurements of the points of intersection (I1, I2, I3, I4) for each wearer, respectively. The zone of use is thus representative of the statistical distribution of the measured points.

Step c)

We will now describe how the statistical distribution of the measurements is used to determine at least one progressive lens optical conception parameter for a wearer.

More precisely, it is sought to determine at least one optical conception parameter among: a value of progression length, a value of internal offset (inset E), a value of working distance or a comfortable position (or even RD for reading distance), and/or input data for a calculation of personalized design.

In FIGS. 4A and 4B, respectively, LP1 and LP2 denote the progression length of the ophthalmic lens, respectively. In the case of FIG. 4A, it is preferable to choose a progression length LP1 longer than the progression length LP2 of FIG. 4B. Ideally, the zone of use ZU extends as far as the lower edge of the frame, without intersecting with the frame so as to prevent partial obstruction of the near-vision visual field.

Method—Step c): First Embodiment of Determination of a Progression Length

A reference line 18 that corresponds to a comfortable mean drop direction of the gaze, preferably equal to 20 degrees, is defined relative to a primary direction (D0) of the far-vision gaze of the wearer.

A difference $\Delta$ is calculated between the reference line 18 and a value representative of the visual behavior of the wearer and that is calculated depending on:

the position of the centroid BU of the zone of use ZU; and/or the high position HU and/or low position LU of the zone of use ZU.

In one embodiment, $\Delta$ is defined as the difference between the vertical position of the centroid (BU) and a reference vertical position (17), corresponding to the mean drop angle of the gaze relative to a primary direction (D0) of the far-vision gaze of the wearer.

The result of the statistical processing in step b) gives a behavioral indication, essentially related to a notion of comfort, that may be translated at the design level by an adjustment of the progression length.

A recommendation is made of a restricted range of progression length Lp (or LOC for length of progression) depending on the sign of $\Delta$.

For example, if $\Delta$ is negative, a rather short restricted range of progression-length values, preferably between 14 and 16 mm, is recommended.

If $\Delta$ is positive, a rather long restricted range of progression-length values, preferably between 16 and 18 mm, is recommended.

Method: Step c) Second Embodiment of Determination of a Progression Length (FIGS. 5 to 10)

In the second embodiment, a difference $\Delta$ is also calculated between the reference line 18 and a value representative of the visual behavior of the wearer, the difference $\Delta$ being calculated depending on:

the position of the centroid BU of the zone of use ZU; and/or the high position HU and/or low position LU of the zone of use ZU.

In one embodiment, $\Delta$ is defined as the difference between the vertical position of the centroid (BU) and a reference vertical position (17), corresponding to the mean drop angle of the gaze relative to a primary direction (D0) of the far-vision gaze of the wearer.

Next, the progression-length value relative to $\Delta$ is adjusted so as to increase the share of the NV zone in the eyeglass by decreasing the value of the progression length (LOC), according to a formula of the type:

$$LOC = FH - \epsilon$$

$\epsilon$ represents a correction function or parameter, which is calculated from one or more elements liable to influence the value of the LOC, these elements possibly being of different natures:

depending on a hardware element that depends on the frame and/or the wear position of the frame by the user such as the fitting height FH, the datum height (Hd) or the rectangle inscribed around the lens (or data boxing);

depending on optical data, such as the refraction of the wearer, which allows prismatic effects to be taken into account;

depending on behavioral aspects, such as the drop of the gaze, the zone of use and the centroid of the zone of use.

This list of elements is in no way limiting.

The various variants of the second embodiment correspond to various ways of determining the value of the parameter ϵ.

FIG. 5 shows a non-edged progressive lens 8 seen from in front. A frame 10 is also shown, having a fitting height limited to less than 14 mm. The fitting cross is here placed at the center of the rectangle circumscribed around the frame 10. The FV zone 11 is located in the upper portion of the eyeglass, but it will be noted that the NV zone 12 of the eyeglass is located outside of the frame. In this case, the result of the method comprises emitting an alarm message to signal an incompatibility between the chosen frame, the measurement, the adjustment and/or the design.

In FIGS. 6-7, the frame 10 has a fitting height FH, which is by way of nonlimiting example, comprised between 14 mm and 17 mm.

FIG. 6 shows the case where the difference Δ is positive, i.e. in which the mean drop of the NV gaze of the wearer is larger than, for example, 20 degrees.

In this variant of the second embodiment, when the difference Δ is positive, a value of the progression length (LOC) is chosen according to a formula of the type:
LOC=FH In other words, the value of ϵ is fixed to ϵ=0.

The center of the NV zone 12 is located on the edge of the frame 10 (cf FIG. 6).

FIG. 7 shows the case where the difference Δ is negative, i.e. in which the mean drop of the NV gaze of the wearer is smaller than 20 degrees. In this variant of the second embodiment, when the difference Δ is negative, a value of progression length (LOC) is chosen according to a formula of the type:

LOC=max(FH−k(FH);14 mm)

0<k(FH)<1.5 mm

In a nonlimiting example, the function k(FH) is an affine function, such that for example: k=0.35×(FH)−5.25

In this second embodiment, a progression length in a long range is favored.

Figure 8:
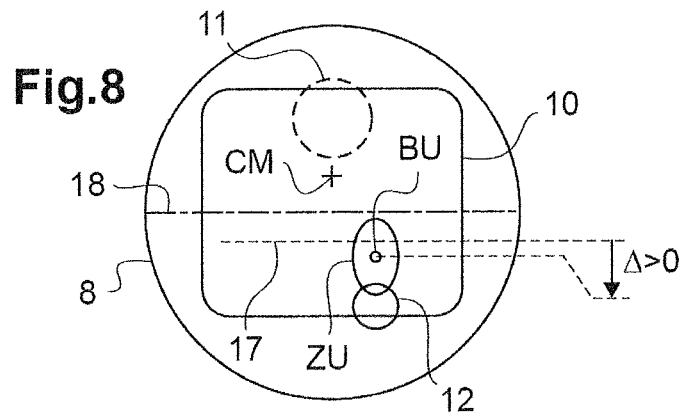
FIG. 8 shows a third variant of the first embodiment for determining a progression length of a progressive lens.
Figure 9:
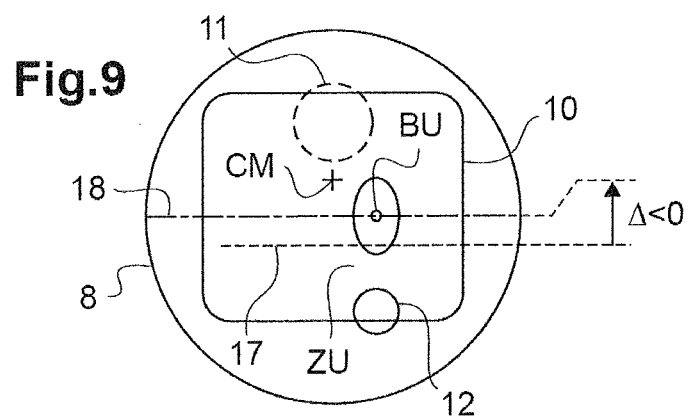
FIG. 9 shows a fourth variant of the first embodiment for determining a progression length of a progressive lens.

In FIGS. 8-9, the frame 10 has a fitting height FH larger than 17 mm.

Figure 10:
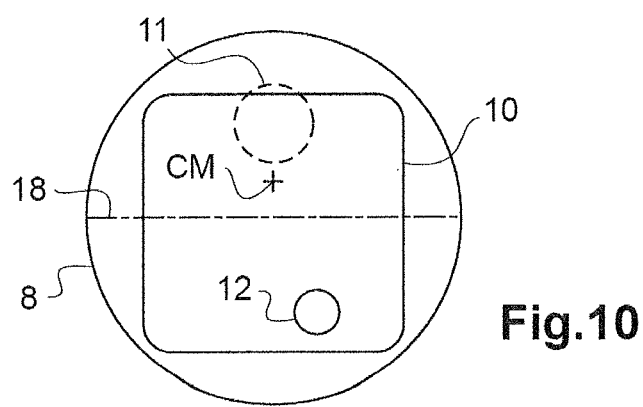
FIG. 10 shows a fifth variant of the first embodiment for determining a progression length of a progressive lens.

In the case where the difference Δ is positive (FIG. 8), a predetermined progression-length value is chosen, for example:
LOC=18 mm In the case where the difference Δ is negative (FIG. 9), a predetermined progression-length value is chosen, for example:
LOC=17 mm FIG. 10 illustrates the case where the frame 10 has a fitting height FH larger than 20 mm. In this case, a progression length in a long range, preferably comprised between 16 and 18 mm, is favored.

Method: Step c) Third Embodiment of Determination of a Progression Length (FIG. 11)

Figure 11:
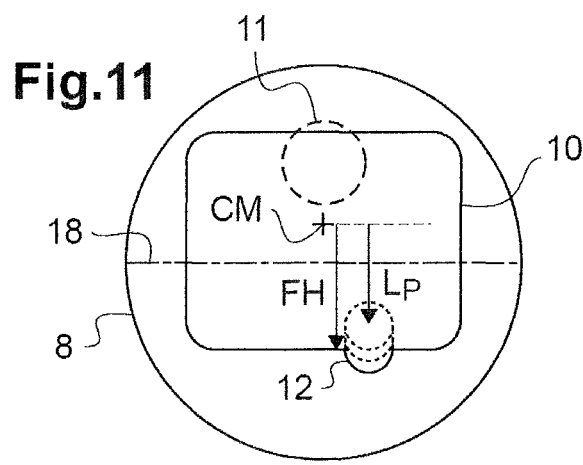
FIG. 11 shows a second embodiment for determining a progression length of a progressive lens.

FIG. 11 illustrates a third embodiment in which the progression length is adjusted depending on the value of the differential Δ between the effective mean drop and a mean gaze drop (typically of 20 degrees).

In one embodiment, Δ is defined as the difference between the vertical position of the centroid (BU) and a reference vertical position (17), corresponding to the mean drop angle of the gaze relative to a primary direction (D0) of the far-vision gaze of the wearer.

In this case, the value of the progression length is calculated depending on the fitting height (FH) and on the value of Δ according to a formula of the type:

LOC=FH−ϵ(FH,Δ)

ϵ represents a correction function or parameter, which is calculated from one or more elements liable to influence the value of the LOC, these elements possibly being of different natures:

depending on a hardware element that depends on the frame and/or the wear position of the frame by the user such as the fitting height FH, the datum height (Hd) or the rectangle inscribed around the lens (or data boxing);

depending on optical data, such as the refraction of the wearer, which allows prismatic effects to be taken into account;

depending on behavioral aspects, such as the drop of the gaze, the zone of use and the centroid of the zone of use.

This list of elements is in no way limiting.

From a calculational point of view, the principle is to place boundaries on Δ and to assign optimal amendment values:

|  |  | FH FH min | FH max |
| --- | --- | --- | --- |
| Δ |  | 14 | 20 |
| Δ min | −3 | 0 | 2 |
| Δ max | 2 | 0 | 3 |

For example, for FH=14 mm no shortening is tolerated whatever the value of the difference Δ. In contrast, for a height FH=20 mm a maximum shortening of 3 mm and a minimum shortening of 2 mm is permitted for values of Δ of 2 and −3 mm, respectively.

These values, integrated into a solver allow us to obtain all the intermediate values by calculation of a transfer function of the type:

ϵ=U+V*Δ+W*FH+X*Δ*FH where for example U=−6.06667; V=60.4667; W=0.43333; and X=0.03333 or

ϵ=U+V*Δ+W*FH+X*Δ*FH+Y*Δ²+Z*FH² where for example U=5.642; V=−0.46667; W=−0.984333; X=0.033; Y=−0.00467; Z=0.041667

The transfer layers represent the transfer function between the space (FH, Δ) and the amendment ϵ to be applied to FH to obtain the progression-length value:

LOC=FH−U+V*Δ+W*FH+X*ΔFH            (VI.11)

LOC=FH−U+V*Δ+W*FH+X*Δ*FH+Y*Δ²+Z*FH²            (VI.12)

The correction function ϵ=k(FH, Δ) may be an affine function, or a more complex function of quadratic type as illustrated above, for a more uniform apportionment of the distribution of progression-length values. It may also be an exponential or logarithmic function.

Advantageously, it is furthermore possible to adjust the correction function by taking into account parameters such as spherical correction Rx, prismatic deviation, design and/or other parameters of the type of compensation associated with the datum fitting height Hd.

This adjustment may be carried out at the level of the value of the LOC or at the level of the expression of the correction function or parameter $\epsilon$.

Method: Step c) Fourth Embodiment of Determination of a Progression Length (FIG. 12)

Figure 12:
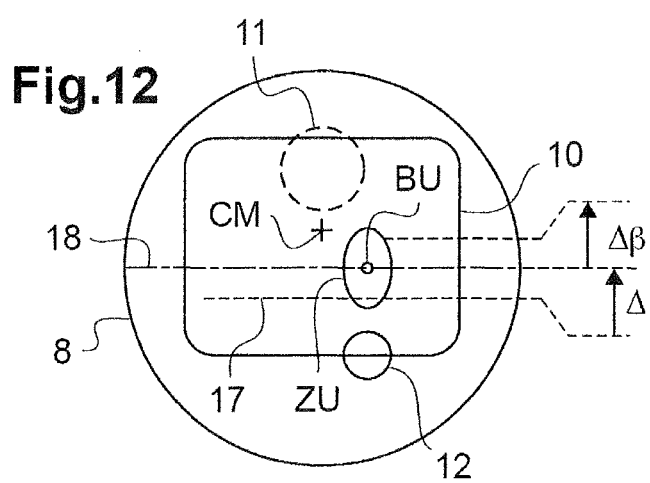
FIG. 12 shows a third embodiment for determining a progression length of a progressive lens.

In this fourth embodiment the progression length is adjusted depending on the difference $\Delta$ between the effective mean drop and the mean gaze drop (for example 20 degrees) and depending on a value representative of the spatial dispersion ($\Delta\beta$, XU, YU) of the zone of use (ZU) (FIG. 12).

This dispersion may be the vertical spread $\Delta\beta$ of the zone of use, the vertical spread YU of the zone of use or the horizontal spread XU of the zone of use.

For example, the vertical spread $\Delta\beta$ is equal to the vertical standard deviation of the statistical distribution.

In one embodiment, $\Delta$ is defined as the difference between the vertical position of the centroid (BU) and a reference vertical position (17), corresponding to the mean drop angle of the gaze relative to a primary direction (D0) of the far-vision gaze of the wearer.

In this case, the value of the progression length is calculated depending on the fitting height (FH) and on the value of $\Delta$ according to a formula of the type:

LOC=FH−$\epsilon$(FH,$\Delta$,ZU)

In one variant embodiment, a transfer function is calculated such that:

LOC=$f$(FH,$\Delta$,$\Delta\beta$)

A calculation is then made on a transfer function of the 3$^{rd}$ order (FIG. 12).

Taking into account the spread of the zone of use especially allows the LOC to be adjusted depending on an eye/head coefficient of the wearer and more particularly depending on the eye/head behavior of the wearer, depending on whether the wearer privileges movements of the head rather than those of the eyes or vice versa. This taking into account of the eye/head behavior of the wearer makes it possible to ensure an optimal visual comfort for this wearer.

Advantageously, it is furthermore possible to adjust these functions by taking into account parameters such as spherical correction Rx, cylindrical correction, prismatic deviation, design and/or parameters of the type of compensation associated with the datum fitting height Hd.

In this case, the correction function of the progression length is written in the form:

LOC=FH−$\epsilon$(FH,$\Delta$)−$F(RX(\ ))$ where RX represents the refraction of the wearer, or even:

LOC=FH−$\epsilon$(FH,$\Delta$,ZU)−$C$(Boxing/Datum)

so as to perform a systematic compensation due to the inherent differential between the measurements of the height of the inscribed rectangle and of the datum height (or Boxing/Datum coefficient).

Of course, a correction function may combine the various parameters for example in the form:

LOC=FH−$\epsilon$(FH,$\Delta$,Use)−$C$(Boxing/Datum)−$F(RX)$

This adjustment may be carried out at the level of the value of the LOC or at the level of the expression of the correction function or parameter $\epsilon$.

Advantageously, it is furthermore possible to adjust these functions by taking into account parameters associated with the cephalic posture of the wearer and/or the bodily posture of the wearer.

Method: Step c) Fifth Embodiment of Determination of a Progression Length (FIG. 13)

Figure 13:
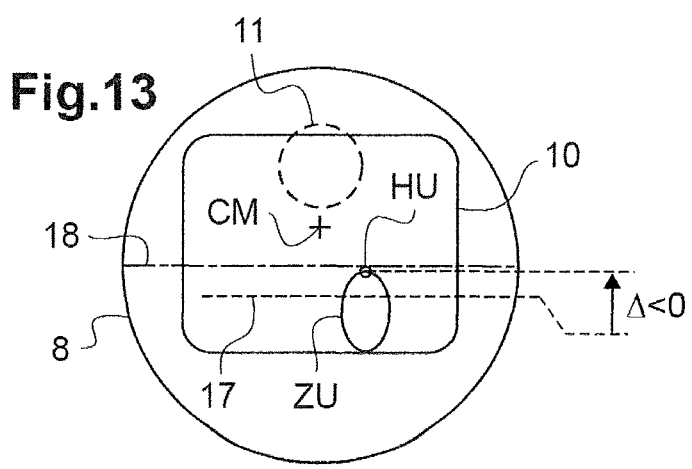
FIG. 13 shows a fourth embodiment for determining a progression length of a progressive lens.

In this fifth embodiment, the progression length is adjusted using the difference $\Delta$ between the high boundary HU of the zone of use ZU and the mean gaze drop (20 degrees) (cf. FIG. 13).

Thus the vertical spread may serve to define a high position HU allowing an optical area to be positioned or the design characteristics thereof to be defined.

Alternatively, it is possible to use the value of $\Delta$ to define field targets for the calculation of a personalized design, such as the location of the NV zone and the extent of the NV zone.

Method: Step c) Sixth Embodiment (FIGS. 14 and 15)

In this sixth embodiment, the results of the statistical distribution are used to determine or to adjust at least one parameter of the optical design.

It is possible to use also in combination or independently:

the position of the centroid BU of the zone of use;

the high limit HU of the zone of use;

the low limit LU of the zone of use;

the nasal limit NU of the zone of use;

the temporal limit TU of the zone of use;

the vertical spread YU of the zone of use;

the horizontal spread XU of the zone of use.

For example, the position in x and/or in y of the centroid BU of the zone of use is used to determine the position in x and/or in y of the point IVP of the progressive lens.

In another example, the high limit HU is used to adjust the progression profile to 85% spherical power addition, which corresponds to the start of the NV zone, by modifying the progression profile of the design so as to deliver a NV zone 12 that is consistent with the visual strategy of the wearer (see FIGS. 15A and 15B). FIG. 15C shows two optical power addition profiles along a meridian line—the dotted line is for a first wearer having a zone of use such as shown in FIG. 15A and the dashed line is for another wearer having a zone of use such as shown in FIG. 15B, respectively. The total addition between the FV zone and the NV zone is for example equal to two diopters for these two wearers. The progression profile is adjusted in a personalized way so that the high limit HU of the zone of use corresponds to a spherical power addition of 85%, i.e. equal to 1.70 diopters. In addition, the progression length is adjusted so that the centroid BU corresponds to an addition of 100%, i.e. forms part of the NV zone.

In another example, the vertical spread YU allows the progression length of the design to be adjusted so as to raise the NV. This correction of the progression length increases in magnitude as the vertical spread YU increases in size in order to provide a large NV zone that is easily accessible and suitable for the visual strategy of the wearer.

In another example, the position of the centroid BU and the vertical spread YU of the zone of use ZU allow the height of the near-vision zone 12 to be determined.

In another example, the nasal limit NU and/or temporal limit TU allow the value of the offset E to be determined.

It is also possible to use the position Y of the centroid BU as a variable of adjustment of the internal offset E.

In another example, the horizontal spread XU allows the field width of the design in the NV zone to be adjusted, by shortening the progression length, using local adjustment layers and/or by directly modifying the power and astigmatism targets during an optimization of the optical design.

Thus, the horizontal spread XU allows a relatively gentle and narrow or in contrast hard and wide design to be chosen from a plurality of predefined designs or in a continuum.

Advantageously, the adjustment of the progression design of the progressive lens takes into account a measurement of eye-head coefficient and/or data related to the natural posture of the wearer in order to ensure him an optimal visual comfort.

Thus, the zone of use may be used as an input parameter in order to complement the correction function.

In addition to the origin parameters, such as the fitting height FH that accounts for the frame and its wear position, and the difference Δ that accounts for the comfortable position of the subject, the addition of a variable of ZU type accounts for the propensity the subject to explore the space during the visual task. This embodiment makes it possible to determine more precisely not only the progression length (LOC) but also a field width in the horizontal direction.

Method: Seventh Embodiment (FIG. 16)

In this embodiment, a set of statistical distributions of visual behavioral measurements relating to a plurality of wearers forming a reference population in the statistical sense is collected. This reference population may be segmented as a function of ametropia, age, the type of wearer or ethnicity.

Thus, a plurality of mean values (mean direction of the gaze of the wearer or mean position of the gaze of the wearer in a projection plane (PM) or mean drop angle of the gaze of the wearer) relating to an area of use (ZU) are provided, said values being associated with the plurality of wearers.

Next, said plurality of mean values associated with said plurality of reference wearers are processed in order to determine a statistical distribution of said plurality of mean values.

For example, FIG. 16 shows points B1, B2, B3, B4 each corresponding respectively, for example, to the centroid of the area of use for visual behavioral measurements of various wearers, such as described in steps a) and b).

For a reference population, statistical processing that for example allows a maximum height and a minimum height to be calculated is carried out.

In a subsequent step, a mean value relating to the area of use (ZU) is determined for a wearer during a visual task.

In the example, the point Bi corresponds to the position of the centroid of the zone of use for a wearer for whom it is sought to personalize the progressive lens.

Next, at least one optical conception parameter is determined for a progressive ophthalmic lens for said wearer depending on said mean value relating to the area of use for said wearer and on said statistical distribution of mean values associated with said plurality of reference wearers.

In the example, a transfer law between the position of the point Bi and the recommended LOC value is determined.

By way of example the transfer law is a linear law, according to a formula of the type:

$$LOC = K\beta + C$$

$$\text{where } K = \frac{18-14}{Maxi-Mini} \text{ and } C = \frac{14.Maxi - 18.Mini}{Maxi - Mini}$$

This embodiment allows bias errors due to various unreliable measurement conditions to be attenuated.

Advantageously, the data relating to the reference population may be updated depending on newly taken measurements.

For example, an apparatus of the type of that sold under the trademark "Visioffice link" may allow an online update of data relating to the reference population.

By virtue of the method for determining optical conception parameters of the invention, it is possible to determine for a given wearer the most suitable progressive ophthalmic lens.

In a first embodiment, this lens is selected depending on the determined optical conception parameter from a standard set of lenses in order to match as well as possible this optical conception parameter.

In a second embodiment, the method for determining lens optical conception parameters may be implemented in the context of an optimization process for optimizing a progressive ophthalmic lens intended for a wearer of known prescription. Here, the expression "optimization process" is understood to mean either a process for calculating ab initio an optical conception design of a progressive ophthalmic lens, or a method for modifying an existing optical design depending on the parameter in question. This modification may be obtained by a modification of the target zones in an optimization calculation, by direct addition of a corrective layer to an eyeglass, by stretching the progression length (LP), or by choosing a design from various progressive ophthalmic lens designs. This optimization makes it possible to get as close as possible to a suitable progressive ophthalmic lens depending on behavioral measurements of the wearer.

This optimization method may comprise a first step of determining initial equations of the front and back surfaces of the lens. These determinations may be carried out by reading data provided by the manufacturer of the ophthalmic lens or by measurement.

Next, at least one current ophthalmic lens surface is chosen. This at least one current surface may be chosen identical to the at least one initial surface of the corresponding lens. However, it is known to those skilled in the art that this at least one current surface may also be chosen different from the at least one initial surface of the corresponding lens. The current surfaces correspond to a back face of the ophthalmic lens, oriented toward the wearer and/or to a front face of the ophthalmic lens, opposite the wearer.

Next, a target optical function and target optical design parameters are determined according to the method of the invention in order to determine, by optimization, under the wear conditions, the current surface of the lens using the determined optical targets.

These targets provide values of power, modulus of astigmatism and axis of astigmatism for given gaze directions.

By way of example, it is possible to determine as targets for the optimization, a target of variation of the power along the meridian and in particular a value of progression length along the meridian determined according to the method of the invention.

The lens according to the invention, thus obtained, therefore meets as well as possible the needs of the wearer and provides him with a better visual comfort.

Advantageously, it may be envisioned to note certain optical conception parameters determined by the process according to the invention on the order form of a pair of ophthalmic lenses usable by an optician. The optical conception parameters are associated with data on near-vision and far-vision prescribed power, prescribed addition, pupillary distances of the wearer, the pantoscopic angle of the frame, the eyeglass-eye distance and data on the frame chosen by the wearer.

For any box not filled in on the order form, the standard mean value used in existing calculation programs is adopted.

On each copy of an order form is noted an optical optimization calculation computer program in order to calculate the pair of lenses and edit the manufacturing order that controls the machining tool.

Moreover, this optimization method may be implemented in a process for manufacturing an ophthalmic lens.

The process for manufacturing an ophthalmic lens comprises a first step of providing an initial ophthalmic lens, optionally a semifinished lens.

The step of determining the optimized surface for the ophthalmic lens by means of the optimization method is followed by a step of machining the lens to produce the at least one optimized surface.

As indicated above, it is possible to optimize one or both surfaces of the lens depending on the circumstances. Likewise, the manufacturing process may be implemented by machining one or both surfaces of the initially provided ophthalmic lens. The machining of the lenses to produce the optimized surface(s) may especially be carried out using what is called a digital surfacing method on a digitally controlled machine-tool suitable for single-face or double-face machining of a progressive ophthalmic lens.

The invention claimed is:

1. A method for determining at least one optical conception parameter for a progressive ophthalmic lens intended to equip a frame of a wearer, depending on the visual behavior of the latter, the method comprising the following steps:
   a) collecting a plurality of behavioral measurements relating to a plurality of gaze directions and/or positions of the wearer during a visual task;
   b) statistically processing said plurality of behavioral measurements in order to determine a zone of use of the area of an eyeglass fitted in said frame, said zone of use being representative of a statistical spatial distribution of said plurality of behavioral measurements;
   c) determining at least one optical conception parameter for said progressive ophthalmic lens depending on a spatial extent and/or position of the zone of use, wherein said at least one optical conception parameter comprises at least one of a restricted progression-length range [Lpmin; Lpmax] and a value of progression length;
   b1) calculating a position of the centroid of the zone of use;
   b2) determining the sign of the difference Δ between the vertical position of the centroid and a reference vertical position, corresponding to a mean drop angle of the gaze relative to a primary direction of the far-vision gaze of the wearer; and
   c2) determining a restricted progression-length range [Lpmin; Lpmax] or a value of progression length depending on the sign of the difference Δ.

2. The method for determining at least one optical conception parameter for a progressive ophthalmic lens of claim 1, wherein said at least one optical conception parameter comprises a height of the near-vision zone, a width of the near-vision zone, and an internal offset of said progressive ophthalmic lens.

3. The method for determining at least one optical conception parameter for a progressive ophthalmic lens of claim 2, further comprising the following steps:
   b7) calculating the position of a limit of the zone of use; and
   c7) determining the value of the internal offset depending on the position of said limit of the zone of use.

4. The method for determining at least one optical conception parameter for a progressive ophthalmic lens of claim 2, further comprising the following steps:
   b8) calculating a position of the centroid of the zone of use and a vertical spread of the zone of use; and
   c8) determining the height of the near-vision zone depending on the position of the centroid of the zone of use and on the vertical spread of the zone of use.

5. The method for determining at least one optical conception parameter for a progressive ophthalmic lens of claim 2, further comprising the following steps:
   b9) calculating a horizontal spread of the zone of use; and
   c9) determining the width of the near-vision zone depending on the horizontal spread of the zone of use.

6. The method for determining at least one optical conception parameter for a progressive ophthalmic lens of claim 1, wherein said at least one optical conception parameter comprises a profile of progression of the optical power along a meridian between the far-vision zone and the near-vision zone for said progressive ophthalmic lens.

7. The method for determining at least one optical conception parameter for a progressive ophthalmic lens of claim 6, further comprising the following steps:
   b6) calculating the position of a limit of the zone of use; and
   c6) determining a progression profile of the optical power along a meridian between the far-vision zone and the near-vision zone depending on the position of said limit of the zone of use.

8. The method for determining at least one optical conception parameter for a progressive ophthalmic lens of claim 1, further comprising the following steps:
   a3) acquiring a measurement of fitting height for said progressive ophthalmic lens in said frame;
   b3) calculating the value of the difference Δ between the vertical position of the centroid and a reference vertical position, corresponding to a mean drop angle of the gaze relative to a primary direction of the far-vision gaze of the wearer; and
   c3) determining a value of progression length depending on said measurement of fitting height and on said value of the difference Δ.

9. The method for determining at least one optical conception parameter for a progressive ophthalmic lens of claim 8, wherein in step c3) a value of progression length is determined, said value being equal to the fitting height decreased by a quantity $\epsilon$ where $\epsilon$ is a function of the difference Δ , of the fitting height, of a measurement of ocular refraction of the wearer and/or of the zone of use.

10. The method for determining at least one optical conception parameter for a progressive ophthalmic lens claim 1, further comprising the following steps:
   a4) acquiring a measurement of fitting height for said progressive ophthalmic lens in said frame;

b4) calculating the value of the difference Δ between the vertical position of the centroid and a reference vertical position, corresponding to a mean drop angle of the gaze relative to a primary direction of the far-vision gaze of the wearer;

b5) calculating at least one value representative of a dispersion of the zone of use; and c5) determining a value of progression length depending on said measurement of fitting height, on said value of the difference Δ and/or on said at least one value representative of a dispersion of the zone of use.

11. The method for determining at least one optical conception parameter for a progressive ophthalmic lens of claim 10, wherein in step c5) a value of progression length is determined, said value being equal to the fitting height decreased by a correction function ε where ε is a function of the difference Δ, of the fitting height and of the dispersion of the zone of use.

12. The method for determining at least one optical conception parameter for a progressive ophthalmic lens of claim 10, further comprising the following steps:
   b9) calculating a horizontal spread of the zone of use; and
   c9) determining the width of the near-vision zone depending on the horizontal spread of the zone of use.

13. The method for determining at least one optical conception parameter for a progressive ophthalmic lens of claim 10, wherein the optical conception parameter is adjusted depending on the spherical-compensation value of the prescription of the progressive ophthalmic lens and/or on the value of the optical-power addition between the far-vision zone and the near-vision zone.

14. The method for determining at least one optical conception parameter for a progressive ophthalmic lens of claim 10, wherein the optical conception parameter is adjusted depending on a measurement of an angle of inclination of the head of the wearer.

15. The method for determining at least one optical conception parameter for a progressive ophthalmic lens of claim 10, wherein:
   d) a plurality of mean values relating to an area of use are provided, said values being associated with a plurality of reference wearers;
   e) said plurality of mean values associated with said plurality of reference wearers are statistically processed in order to determine a statistical distribution of said plurality of mean values;
   f) a mean value relating to the area of use is determined for a wearer during said visual task; and
   g) at least one optical conception parameter is determined for a progressive ophthalmic lens for said wearer depending on said mean value relating to the area of use for said wearer and on said statistical distribution of mean values associated with said plurality of reference wearers.

16. The method for determining at least one optical conception parameter for a progressive ophthalmic lens of claim 1, wherein the optical conception parameter is adjusted depending on the spherical-compensation value of the prescription of the progressive ophthalmic lens and/or on the value of the optical-power addition between the far-vision zone and the near-vision zone.

17. The method for determining at least one optical conception parameter for a progressive ophthalmic lens of claim 1, wherein the optical conception parameter is adjusted depending on a measurement of an angle of inclination of the head of the wearer.

18. The method for determining at least one optical conception parameter for a progressive ophthalmic lens of claim 1, wherein:
   d) a plurality of mean values relating to an area of use are provided, said values being associated with a plurality of reference wearers;
   e) said plurality of mean values associated with said plurality of reference wearers are statistically processed in order to determine a statistical distribution of said plurality of mean values;
   f) a mean value relating to the area of use is determined for a wearer during said visual task; and
   g) at least one optical conception parameter is determined for a progressive ophthalmic lens for said wearer depending on said mean value relating to the area of use for said wearer and on said statistical distribution of mean values associated with said plurality of reference wearers.

19. A method for manufacturing a progressive ophthalmic lens comprising:
   providing an initial lens;
   determining the progressive ophthalmic lens by implementing the method for determining at least one optical conception parameter for a progressive ophthalmic lens of claim 1; and
   machining the initial lens in order to produce said progressive ophthalmic lens.

* * * * *